United States Patent [19]

Deguchi et al.

[11] Patent Number: 4,948,560
[45] Date of Patent: Aug. 14, 1990

[54] OXYGENATOR

[75] Inventors: Hiromi Deguchi, Shizuoka; Kiyotaka Nagayama, Unoke, both of Japan

[73] Assignee: Terumo Corporation, Tokyo, Japan

[21] Appl. No.: 352,650

[22] Filed: May 12, 1989

Related U.S. Application Data

[63] Continuation of Ser. No. 801,773, Nov. 26, 1985, abandoned.

[30] Foreign Application Priority Data

Nov. 27, 1984 [JP] Japan .................................. 59-250259

[51] Int. Cl.$^5$ ............................................. A61M 1/03
[52] U.S. Cl. .................................... 422/48; 210/321.8;
210/321.89; 55/18; 55/20; 55/267; 128/DIG. 3; 261/DIG. 28
[58] Field of Search ................. 422/46, 48; 210/321.8, 210/321.89; 55/18, 20, 267; 128/DIG. 3; 261/DIG. 28

[56] References Cited

U.S. PATENT DOCUMENTS

| | | |
|---|---|---|
| 3,927,981 | 12/1975 | Vianney et al. |
| 4,239,729 | 12/1980 | Hasegawa et al. ................. 422/48 |
| 4,283,284 | 8/1981 | Schnell ............................. 210/321.3 |
| 4,374,802 | 2/1983 | Fukasawa ............................. 422/48 |
| 4,376,095 | 3/1983 | Hasegawa ............................. 422/46 |
| 4,414,110 | 11/1983 | Geel et al. ......................... 422/48 X |

FOREIGN PATENT DOCUMENTS

| | | |
|---|---|---|
| 0048943 | 4/1982 | European Pat. Off. |
| 0089122 | 9/1983 | European Pat. Off. |
| 0089748 | 9/1983 | European Pat. Off. |
| 2343845 | 3/1974 | Fed. Rep. of Germany |

Primary Examiner—Robert J. Warden
Assistant Examiner—Lynn M. Kummert
Attorney, Agent, or Firm—Cushman, Darby & Cushman

[57] ABSTRACT

An oxygenator has a housing provided with a blood inlet and a blood outlet, a bundled aggregate of a multiplicity of gas-exchange membranes, and a gas inlet and a gas outlet independently formed outside opposite bundle end parts of the bundled membrane aggregate, the bundled membrane aggregate being stowed within the housing in such a manner as to partition a gas flow path for communication between the gas inlet and gas outlet and a blood flow path for communication between the blood inlet and blood outlet from each other, which oxygenator is characterized by the fact that the bundled membrane aggregate is provided in or near the gas outlet with a device for thermally insulating or heating the gas emanating from the gas outlet.

7 Claims, 1 Drawing Sheet

OXYGENATOR

This application is a continuation of U.S. application Ser. No. 801,773, filed Nov. 26, 1985, now abandoned.

BACKGROUND OF THE INVENTION

1. Field of the Invention:

This invention relates to an oxygenator to be used for external circulation. More particularly, this invention relates to an oxygenator improved to delay amply the loss of gas-exchange capacity by aging.

2. Description of Prior Art:

The conventional oxygenators are broadly grouped under two types, the bubble type and the membrane type. Recently, the oxygenators of the membrane type which have a less adverse effect on the blood than those of the bubble type have come to find more popular utility. The membrane type oxygenators operate on the principle that exchange of oxygen gas for carbon dioxide gas in blood is effected through the medium of a gas-exchange membrane such as, for example, a membrane made of porous synthetic resin when the oxygen gas is supplied to one side and the blood to the other side respectively of the gas-exchange membrane.

The oxygenators of this type, however, have the drawback that their gas-exchange capacity is gradually degraded after protracted use. To be more specific, this degradation of the gas-exchange capacity proceeds as the water in the blood permeates the membrane, leaks into the oxygen gas, and transforms into steam, this steam is condensed into water drops on exposure to a cool ambient air, and the water drops wet the surface of the membrane. This phenomenon is called a "wet lung."

For the purpose of enabling the water drops adhering to the surface of the membrane to fall down easily, it has been proposed to change the shape of the housing for the oxygenator or to change the material for the membrane. The improvements so proposed, however, do not overcome the drawback perfectly.

An object of this invention, therefore, is to provide a novel oxygenator for blood.

Another object of this invention is to provide an oxygenator so improved as to mitigate notably the loss of the gas-exchange capacity by aging.

SUMMARY OF THE INVENTION

The objects described above are accomplished by an oxygenator, comprising a housing provided with a blood inlet and a blood outlet, a bundled aggregate of a multiplicity of gas-exchange membranes, and a gas inlet and a gas outlet independently formed outside opposite bundle end parts of the bundled membrane aggregate, the bundled membrane aggregate being stowed within the housing in such a manner as to partition a gas flow path for communication between the gas inlet and gas outlet and a blood flow path for communication between the blood inlet and blood outlet from each other, which oxygenator is characterized by the fact that the bundled membrane aggregate is provided in or near the gas outlet side bundle end part thereof with means for thermally insulating or heating the gas emanating from the gas outlet.

This invention further provides as one embodiment thereof an oxygenator wherein the bundled membrane aggregate comprises a multiplicity of gas-exchange hollow fiber membranes and diaphragms for supporting the opposite ends of the hollow fibers fast to the housing.

This invention provides as another embodiment thereof an oxygenator wherein the thermal insulating means is a foam material disposed on the external wall surface forming the gas outlet in such a manner as to coat the external wall surface.

This invention provides as still another embodiment thereof an oxygenator wherein the heating means comprises a heat wire and power supply means therefor both embedded near the gas outlet.

This invention provides as yet another embodiment thereof an oxygenator wherein the gas-exchange membranes are made of hollow fiber bundles.

This invention provides as a further embodiment thereof an oxygenator wherein the gas-exchange membranes are flat membranes superposed so as to give rise to a laminar flow path.

DESCRIPTION OF PREFERRED EMBODIMENT

Now, the present invention will be described below with reference to the working examples illustrated in the accompanying drawings.

Figure 1:
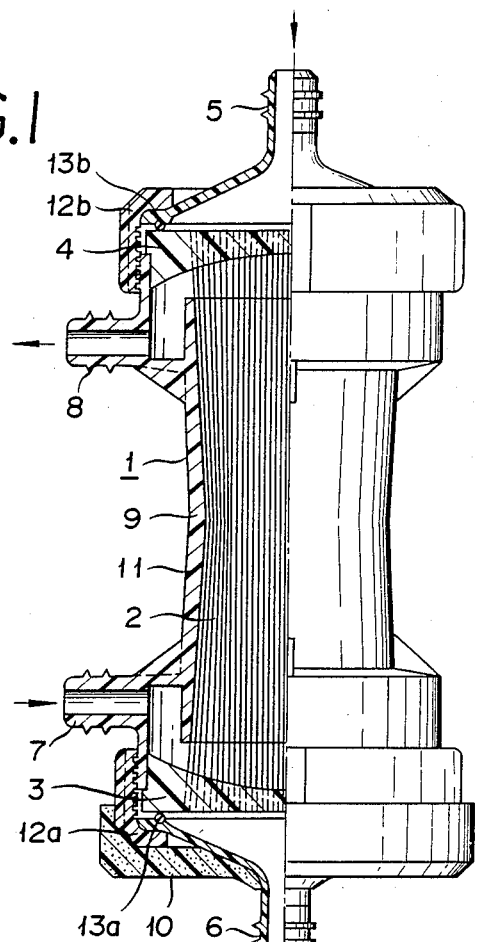
FIG. 1 is a half cutaway front view of a hollow fiber type oxygenator as one preferred embodiment of the present invention.

FIG. 1 is a half cutaway front view of a hollow fiber type oxygenator. This oxygenator is provided with a housing 1, a hollow fiber bundle 2 constituting a bundled aggregate of gas-exchange membranes, two diaphragms 3 and 4, a gas inlet port 5 constituting a gas inlet, a gas outlet port 6 constituting a gas outlet, a blood inlet 7, a blood outlet 8, and a raised constricting part 9.

The housing 1 is in a substantially cylindrical shape and is disposed upright in the axial direction thereof.

The hollow fiber bundle 2 is formed of a multiplicity of gas-exchange hollow fiber membranes disposed inside the housing 1 along the longitudinal direction of the housing 1. The hollow fiber bundle 2 is made of the resin of a polyolefin such as polypropylene or polyethylene and is possessed of numerous pores penetrating through the hollow fiber walls. Properly, in view of gas exchange efficiency, strength, and process of manufacture, the hollow fiber membranes forming the hollow fiber bundle 2 have an inside diameter in the range of about 100 to 1,000 $\mu$m, preferably 100 to 300 $\mu$m, and a wall thickness in the range of about 10 to 50 $\mu$m and the pores in the hollow fiber membranes have an average diameter in the range of about 200 to 2,000 Å and a porosity in the range of 20 to 80%. Unlike the silicone rubber membranes which permit solution and dispersion of a gas, the hollow fiber membranes permit a gas to move in volume flow through the pores and, therefore, are characterized by offering only small resistance to the movement of a gas and enjoying a very high gas-exchange capacity. Of these hollow fiber membranes, those which are destined to contact the blood may be coated with a layer, about 1 to 20 $\mu$m in thickness, of such an antithrombic substance as polyalkyl sulfon, ethyl cellulose, or polydimethyl siloxane.

The diaphragms 3 and 4 are watertightly supported fast at the opposite end parts of the hollow fiber membranes in such a manner as to avoid blocking the cavities of the hollow fiber membranes. They form a blood chamber 11 jointly with the internal wall surface of the housing and the external wall surfaces of the hollow fiber membranes. These diaphragms 3 and 4 are formed of a high molecular weight potting agent such as polyurethane, silicone resin, or epoxy resin. The pressure loss entailed by the circulation of the blood can be decreased by utilizing as the blood chamber the space which is defined by the internal wall surface of the housing and the external wall surfaces of the hollow fiber membranes and the partitions. This setup is desirable because it permits the so-called head perfusion.

The gas inlet port 5 and the gas outlet port 6 are each formed in the shape of a funnel and are allowed to communicate with the internal cavities of the hollow fiber membranes outside the diaphragms 3 and 4. The gas inlet port 5 and the gas outlet port 6 are airtightly attached to the end faces of the housing 1 respectively with annular threaded fasteners 12a and 12b and O-rings 13a and 13b. Instead of using the gas outlet port 6 as described above, the diaphragm 3 side bundle end part of the hollow fiber membranes may be completely left open to serve as a gas outlet.

The blood inlet 7 and blood outlet 8 are disposed respectively in the upper side and the lower side on one lateral side of the housing 1 and allowed to communicate with the blood chamber 11.

Near the gas outlet port 6, thermally insulating means 10 is disposed so as to cover the funnel-shaped portion of the gas outlet port 6 and the head portion of the annular fastener 12a. The thermally insulating means 10 is formed of a heat insulator such as a synthetic resin foam as foamed polystyrene, foamed polyurethane, foamed polyethylene, foamed urea resin, or foamed phenol resin. The thermally insulating means 10 can be fastened in position by adhesion or some other similar means. When the thermally insulating means 10 is formed in the shape of a cap, it may be set fast in position by insertion. Although the thickness of the heat insulator is variable with the kind of material used, it generally falls in the range of 2 to 100 mm, preferably 5 to 30 mm. Since the neighborhood of the gas outlet port 6 which is most susceptible of the phenomenon of wet lung is kept warm because of the presence of the thermally insulating means 10, the otherwise inevitable condensation of steam in the current of gas can be substantially completely precluded. Optionally, the thermally insulating means 10 may be incorporated integrally into the annular fastener 12a or into the gas outlet port.

Figure 2:
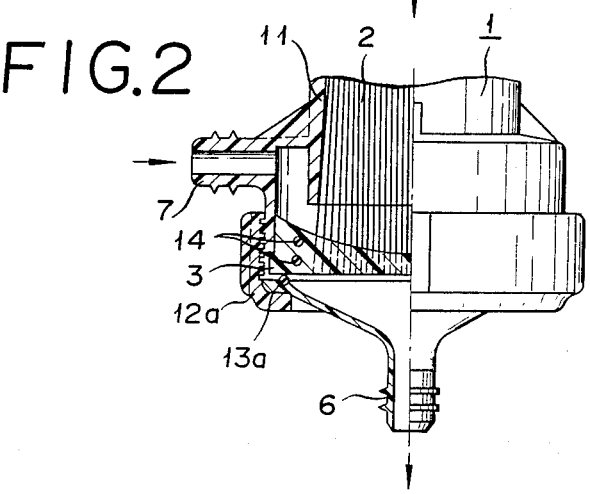
FIG. 2 is a half cutaway view of the essential part of a hollow fiber type oxygenator as another preferred embodiment of the present invention.

FIG. 2 illustrates another working example of this invention. Instead of the thermally insulating means 10 of a foamed material used in the embodiment of FIG. 1, the embodiment of FIG. 2 makes use of heating means which comprises a heat wire 14 embedded within the gas outlet port 6 side partition in such a manner as to enclose the hollow fiber bundle 2 and power supply means (such as, for example, a DC power source) (not shown) adapted to feed electric current to the heat wire. As the heat wire 14 is energized by the power supply means, it generates heat and warms the gas outlet port 6 side partition enough for preventing the steam in the current of gas from being condensed into water drops.

In the embodiment of FIG. 2, since all the other components are identical to those used in the embodiment of FIG. 1. In FIG. 2, therefore, the components which have equivalents in the embodiment of FIG. 1 are denoted by the same numerical symbols. The Explanations on these components are omitted.

Optionally, the heating just described may be effected by embedding a serpentine pipe instead of the heat wire and passing a heat medium through the serpentine pipe.

In either of the foregoing embodiments, the oxygenator has been described as incorporating therein the thermally insulating means or heating means disposed exclusively near the gas outlet port 6 which is most susceptible of the phenomenon of wet lung. Optionally, such thermally insulating means or heating means may be disposed elsewhere in the artificial lung or even throughout the entire length of the artificial lung.

Further, in the foregoing embodiments, the oxygenator has been described as using gas-exchange membranes of hollow fibers. Even in the case of an oxygenator using a multiplicity of flat gas-exchange membranes in a superposed form, the condensation of steam in the current of gas, i.e. the phenomenon of wet lung, can be precluded by having such thermally insulating means as illustrated in FIG. 1 or heating means (heat wire 14) as illustrated in FIG. 2 disposed at least on the gas outlet port side.

(Example of Experiment)

A hollow fiber type oxygenator constructed as illustrated in FIG. 1 was tested for time-course change of gas-exchange capacity. In this case, foamed polystyrene (expansion ratio 40 times) was formed as a heat insulator (thermally insulating means 10) in an average thickness of 10 mm only on the gas outlet 6 side as illustrated.

For comparison, the same hollow fiber type oxygenator, though in a state not provided with the heat insulator, was subjected to the same test. The results are shown in the following table. The data given in the table represent averages each of the values obtained in a set of five measurements.

In this test, bovine blood having the hematocrit value adjusted to 35% was circulated at 37° C., with the blood flow volume at 6 liters/min. and the gas flow volume at 12 liters/min. The oxygen saturation degree of this blood at the inlet of the oxygenator was about 60% and the carbon dioxide gas partial pressure was about 50 mmHg. As hollow fibers, this oxygenator used 4,600 polypropylene porous hollow fibers having an inside diameter of about 200 $\mu$m and a wall thickness of about 25 $\mu$m and containing pores of an average diameter of 500 Å at a porosity of about 50% were used. The hollow fiber membranes aggregated in a bundle had a surface area of 2.5 m$^2$.

Immediately after start of circulation and after 6 hours' circulation, the oxygenator was tested for oxygen addition capacity and for carbon dioxide removal capacity. The results are shown in the following table.

TABLE

|  |  | Immediately after start of circulation | After 6 hours' circulation |
|---|---|---|---|
| Oxygenator of this invention | Oxygen addition capacity (ml/min.) | 270 ± 5 | 265 ± 5 |
|  | Carbon dioxide removal capacity (ml/min.) | 300 ± 8 | 290 ± 6 |
| Comparative experiment (no heat insulator) | Oxygen addition capacity (ml/min.) | 270 ± 5 | 220 ± 20 |
|  | Carbon dioxide removal capacity | 300 ± 10 | 105 ± 40 |

TABLE-continued

|  | Immediately after start of circulation | After 6 hours' circulation |
| --- | --- | --- |
| (ml/min.) | | |

As noted from the foregoing table, the test has demonstrated that the oxygenator of this invention suffers from only small loss of gas-exchange capacity by aging and manifests a high effect in preventing the phenomenon of wet lung.

Now, the operation of the membrane type oxygenator of the present invention will be explained with reference to the experiment described above. An external path for circulation (not shown) is set in place by connection to the blood inlet 7 and the blood outlet 8 and a physiologically harmless liquid (such as, for example, physiologic saline) is circulated through the path until the air entrapped within the blood chamber of the membrane type oxygenator is removed, and then the blood is circulated through the path. The blood is introduced through the blood inlet 7 and discharged through the blood outlet 8 disposed in the upper part of the oxygenator. A feed unit (not shown) for a gas (mixture of air with a suitable amount of oxygen) and a circuit (not shown) adapted to communicate with the feed unit are attached to the gas inlet 5. The gas is introduced through the gas inlet 5 and discharged through the gas outlet 6. The artificial lung of the present invention is adapted so that the blood flows outside the hollow fiber membranes and the gas inside the membranes. Through the medium of these hollow fiber membranes, the removal of carbon dioxide from the blood and the addition of oxygen thereto are effected. Further in this invention, since the means for keeping warm or heating the gas emanating from the gas outlet is disposed near the gas outlet side end part of the bundled aggregate of gas-exchange membranes, the phenomenon that water condensate forms near the gas outlet side end part of the bundled aggregate of gas-exchange membranes when the gas flowing out of the gas outlet is suddenly cooled on contact with the ambient air is precluded. Thus, the loss of the surface area of the gas-exchange membranes owing to the deposition of the water condensate and the clogging of the hollow fiber membranes are prevented and, as the result, the oxygenator is enabled to manifest its gas-exchange ability over a very long period.

As described in detail above, the oxygenator of this invention, despite its very simple construction, avoids entailing the condensation of water in the gas near the gas outlet and the phenomenon of "wet lung" and suffers from very small loss of the gas-exchange property by aging. It can be effectively utilized for protracted auxiliary blood circulation in a patient of imperfect respiration.

What is claimed is:

1. An oxygenator comprising:
   a housing;
   blood inlet means for allowing blood to enter said housing;
   blood outlet means for allowing blood to exit said housing;
   a bundled aggregate of a multiplicity of gas-exchange hollow fiber membranes mounted within said housing, said fiber membranes each having an opening at each end thereof;
   partition members supporting both ends of said bundled aggregate of hollow fiber membranes within said housing without closing the openings of said hollow fiber membranes;
   a gas inlet side header;
   gas inlet means for allowing gas to enter said hollow fiber membranes;
   a gas outlet side header;
   gas outlet means for allowing gas to exit said hollow fiber membranes;
   said partition members being disposed between said inlet and outlet side headers, both said gas inlet means and said gas outlet means being in communication with the interiors of said hollow fiber membranes, said bundled aggregate of hollow fiber membranes being provided so as to separate a gas flow path within said housing through said hollow fiber membranes between said gas inlet means and said gas outlet means and a blood chamber defined between an inner wall of said housing, an outer wall of said hollow fiber membranes, and said partition members and in communication with said blood inlet means and said blood outlet means;
   means for coupling said gas outlet side header to said housing; and
   thermally insulating means in the shape of a cap and wrapped around a portion of an exterior surface of said for coupling and a substantial portion of an external wall surface forming said gas outlet side header formed by an insulating material provided so as to cover said gas outlet side header without preventing gas flow from said outlet,
   whereby the temperature of gas flowing toward and through said gas outlet means is maintained and condensation is minimized.

2. An oxygenator according to claim 1, wherein said thermally insulating means is made of synthetic resin foam.

3. An oxygenator according to claim 2, wherein said synthetic resin foam is foamed polystyrene.

4. An oxygenator according to claim 1, wherein said means for coupling said gas outlet side header to said housing includes an annular threaded fastener.

5. A process for eliminating carbon dioxide from blood and adding oxygen to the blood under external circulation which comprises the steps of:
   providing a housing, blood inlet means for allowing blood to enter said housing, blood outlet means for allowing blood to exit said housing, a bundled aggregate of a multiplicity of gas-exchange hollow fiber membranes mounted within said housing, said fiber membranes each having an opening at each end thereof, partition members supporting both ends of said bundled aggregate of hollow fiber membranes within said housing without closing the openings of said hollow fiber membranes, a gas inlet side header, gas inlet means for allowing gas to enter said hollow fiber membranes, a gas outlet side header, gas outlet means for allowing gas to exit said hollow fiber membranes, said partition members being disposed between said inlet and outlet side headers, both said gas inlet means and said gas outlet means being in communication with the interiors of said hollow fiber membranes, said bundled aggregate of hollow fiber membranes being provided so as to separate a gas flow path within said housing through said hollow fiber membranes between said gas inlet means, and a blood chamber defined between an inner wall of said housing, an outer wall of said hollow fiber membranes, and said partition members and in communication with said blood inlet means and said blood outlet means, and means for coupling said gas outlet side header to said housing;

providing a thermally insulating means in the shape of a cap and wrapping the cap around a portion of an exterior surface of said means for coupling and a substantial portion of an external wall surface of said gas outlet side header formed by an insulating material provided so as to cover said gas outlet side header without preventing gas flow from said gas outlet;

passing the blood into the blood inlet means of said housing;

passing the blood through the blood chamber within said housing;

feeding air containing oxygen into said gas inlet means and through gas flow path formed by the interior of said hollow fiber membranes;

contacting said blood with said air through said hollow fiber membranes to remove carbon dioxide in the blood and add oxygen to the blood; and discharging the gas flowing through said hollow fiber membranes and through said gas outlet means under thermally insulating conditions by means of said thermally insulating means, whereby the temperature of gas flowing toward and through said gas outlet means is maintained and condensation is minimized.

6. A method according to claim 5, wherein said step of providing thermally insulating means comprises providing insulating material which is a synthetic resin foam.

7. A method according to claim 6, wherein said synthetic resin foam is foamed polystyrene.

* * * * *